United States Patent
Burns

(10) Patent No.: US 8,232,057 B2
(45) Date of Patent: Jul. 31, 2012

(54) **DNA SEQUENCES FOR THE DETECTION OF AND DIFFERENTIATION AMONGST PATHOGENIC *E. COLI***

(75) Inventor: Frank R. Burns, Philadelphia, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 1040 days.

(21) Appl. No.: 11/579,483

(22) PCT Filed: Jun. 24, 2005

(86) PCT No.: PCT/US2005/022542
§ 371 (c)(1),
(2), (4) Date: Nov. 3, 2006

(87) PCT Pub. No.: WO2006/012323
PCT Pub. Date: Feb. 2, 2006

(65) Prior Publication Data
US 2009/0068647 A1   Mar. 12, 2009

(51) Int. Cl.
*C12Q 1/68* (2006.01)
*C07H 21/04* (2006.01)
*C12N 9/00* (2006.01)

(52) U.S. Cl. .... 435/6.12; 435/91.2; 435/183; 536/24.33

(58) Field of Classification Search ................ None
See application file for complete search history.

(56) References Cited

U.S. PATENT DOCUMENTS

| | | | |
|---|---|---|---|
| 5,654,417 A | 8/1997 | Tarr et al. | |
| 6,492,113 B1 * | 12/2002 | Vojdani | 435/6 |
| 2002/0058258 A1 * | 5/2002 | Wittwer et al. | 435/6 |
| 2003/0050470 A1 * | 3/2003 | An et al. | 536/24.3 |
| 2004/0110251 A1 * | 6/2004 | Grabowski et al. | 435/69.1 |

FOREIGN PATENT DOCUMENTS

| | | |
|---|---|---|
| WO | WO 00/77247 A1 | 12/2000 |
| WO | WO 0166799 A2 * | 9/2001 |
| WO | WO 02053771 A2 * | 7/2002 |

OTHER PUBLICATIONS

GenBank GI:13400021 [online] Jan. 25, 2001 [retrieved on Apr. 24, 2009] retrieved from http://www.ncbi.nlm.nih.gov/nuccore/13400021 (3 pages).*

Perelle et al., Detection by 5'-Nuclease PCR of Shiga-Toxin Producing *Escherichia coli* 026, 055, 091, 0103, 0111, 0113, 0145 and 015:H7, Associated with the World's Most Frequent Clinical Cases, Molecular and Cellular Probes, 2004, vol. 18:185-192.

International Search Report Dated Nov. 28, 2005, International Application No. PCT/US2005/022542, International Filing Date: Jun. 24, 2005.

Hayashi T et al., Complete genome sequence of enterohemorrhagic *Escherichia coli* O157:H7 and genomic comparison with a laboratory strain K-12. DNA Res. Feb. 28, 2001;8(1):11-22. (USA).

Perna NT et al., Genome sequence of enterohaemorrhagic *Escherichia coli* O157:H7., Nature. Jan. 25, 2001;409(6819):529-33 (UK).

Perna et al., NCBI Reference Sequence NP_290921.1, putative helicase [*Escherichia coli* O157:H7 EDL933], Sep. 28, 2001.

Heung LJ. et al. ,Unlocking the DEAD-box: a key to cryptococcal virulence?, J Clin Invest. Mar. 2005;115(3):593-5.

Bijlsma JJ et al., Identification of virulence genes of *Helicobacter pylori* by random insertion mutagenesis., Infect Immun. May 1999;67 (5):2433-40.

Roos S. et al., Autoaggregation of *Lactobacillus reuteri* is mediated by a putative DEAD-box helicase. Mol Microbiol. Apr. 1999;32(2):427-36.

File History of U.S. Appl. No. 09/980,706, Office Action mailed Nov. 21, 2003.

Liebana, et al. 2003. Genetic diversity among *Escherichia coli* O157:H7 isolates from bovines living on farms in England and Wales. J. Clin. Microbiol. 41:3857-3860.

Wu, G., B. et al. 2008. Genetic diversity among *Escherichia coli* O157:H7 isolates and identification of genes linked to human infections. Infect. Immun. 76:845-856.

* cited by examiner

*Primary Examiner* — Samuel Woolwine

(57) ABSTRACT

Oligonucleotide sequences and methods for specifically detecting and differentiating amongst pathogenic *E. coli* in a complex sample. The complex sample can be a food sample, water sample, or selectively enriched food matrix. The methods of detection may utilize PCR amplification with, or without, an internal positive control, and appropriate primer pairs. Reagents for performing the methods can be supplied as a kit and/or in tablet form.

22 Claims, 5 Drawing Sheets

Mechanism of melting curve analysis

Data Transformation

Raw Data

Processed Data

Data transformations involve the following:

1. Interpolate data to get evenly spaced data points
2. Take log of fluorescence (F)
3. Smooth log F
4. Calculate -d(log F)/dT   $-d_F/d_T$
5. Reduce data to 11-13 data points spaced one degree apart depending on the target organism MELTING CURVE FOR MULTI TARGET PCR, INTERNAL POSITIVE CONTROL, SEQ ID NO:4 AMPLIFIED WITH PS2 AND SEQ ID NO:7 AMPLIFIED WITH PS4

SEQUENCE LISTING

<160> NUMBER OF SEQ ID NOS: 17

<210> SEQ ID NO 1
<211> LENGTH: 138
<212> TYPE: DNA
<213> ORGANISM: Escherichia coli
<220> FEATURE:
<221> NAME/KEY: misc_feature
<222> LOCATION: (1)..(138)
<223> OTHER INFORMATION: specific for serotypes O157:H7, O157:HNM,
      O55:H7, O26:H11, or O145HNM

<400> SEQUENCE: 1
acaatactcg tactttcgaa agttcgctaa ccaggtgcta cacgcgaggt gttgcagttt      60
tctttacgat ttatcattca atcctaatcc atgcatgaca tgtggtgcct gtggggtgat     120
cctacctacg taatgtgg                                                   138

<210> SEQ ID NO 2
<211> LENGTH: 27
<212> TYPE: DNA
<213> ORGANISM: Escherichia coli
<220> FEATURE:
<221> NAME/KEY: misc_feature
<222> LOCATION: (1)..(27)
<223> OTHER INFORMATION: 5' PCR primer for SEQ ID NO:1

<400> SEQUENCE: 2
acaatactcg tactttcgaa agttcgc                                          27

<210> SEQ ID NO 3
<211> LENGTH: 24
<212> TYPE: DNA
<213> ORGANISM: Escherichia coli
<220> FEATURE:
<221> NAME/KEY: misc_feature
<222> LOCATION: (1)..(24)
<223> OTHER INFORMATION: 3' PCR primer for SEQ ID NO:1

<400> SEQUENCE: 3
ccacattacg taggtaggat cacc                                             24

<210> SEQ ID NO 4
<211> LENGTH: 464
<212> TYPE: DNA
<213> ORGANISM: Escherichia coli
<220> FEATURE:
<221> NAME/KEY: misc_feature
<222> LOCATION: (1)..(464)
<223> OTHER INFORMATION: specific for serotypes O157:H7, O157:HNM,
      O55:H7, O26:H11, O26:HNM, O145HNM, or O111HNM

<400> SEQUENCE: 4
caaggcgatt ctttgtcttc ttgcactaat tttttatcat aaaaatgttc ctagcactgg      60
gcatcaatat cgcaggtcag aaagagctcc tggggatgcg gctggccgaa aatgaagggg     120
cgaatttctg gttcaatgtg ctgactgaac tgaaaaaccg cggtctgaac gatatcctca     180
tcgcctgtgt gtatggcctg aaagaattcc cggaggcccg catccagtta tgcatcgtgc     240
atatggtgcg caacagcatg cgcttcgtgt catggaagga atacaaagcc gtcactcgcg     300
acctgaaagc gattagcctc ccacagaaga ggcaggccag caggcactgg aagcgtttgc     360
tgcggcctgg gactgccgct atccgcagat aagccggtgc tagctgtcaa actggactaa     420
cttggcgacg ttttcgctt atccggcaga tatccgcaaa gtga                       464

```
<210> SEQ ID NO 5
<211> LENGTH: 26
<212> TYPE: DNA
<213> ORGANISM: Escherichia coli
<220> FEATURE:
<221> NAME/KEY: misc_feature
<222> LOCATION: (1)..(25)
<223> OTHER INFORMATION: 5' PCR primer for SEQ ID NO:4

<400> SEQUENCE: 5
caaggcgatt ctttgtcttc ttgcac                                          26

<210> SEQ ID NO 6
<211> LENGTH: 27
<212> TYPE: DNA
<213> ORGANISM: Escherichia coli
<220> FEATURE:
<221> NAME/KEY: misc_feature
<222> LOCATION: (1)..(27)
<223> OTHER INFORMATION: 3' PCR primer for SEQ ID NO:4

<400> SEQUENCE: 6
tcactttgcg gatatctgcc ggataag                                         27

<210> SEQ ID NO 7
<211> LENGTH: 163
<212> TYPE: DNA
<213> ORGANISM: Escherichia coli
<220> FEATURE:
<221> NAME/KEY: misc_feature
<222> LOCATION: (1)..(162)
<223> OTHER INFORMATION: specific for serotypes O157:H7, O157:HNM, or
      O55:H7

<400> SEQUENCE: 7
tattaagaga ttgcaaagac attaagggtg gggtgaagag gaaaagaaag aaggttgcgt      60
taaacacatg ttatatagaa gaagtgcttg catcctgctc agagcttggg tttcgaactg     120
acaaaatgaa aaatttaaca cagatttaat tcatgctctt gcc                      163

<210> SEQ ID NO 8
<211> LENGTH: 29
<212> TYPE: DNA
<213> ORGANISM: Escherichia coli
<220> FEATURE:
<221> NAME/KEY: misc_feature
<222> LOCATION: (1)..(29)
<223> OTHER INFORMATION: 5' PCR primer for SEQ ID NO:7

<400> SEQUENCE: 8
tattaagaga ttgcaaagac attaagggt                                       29

<210> SEQ ID NO 9
<211> LENGTH: 25
<212> TYPE: DNA
<213> ORGANISM: Escherichia coli
<220> FEATURE:
<221> NAME/KEY: misc_feature
<222> LOCATION: (1)..(25)
<223> OTHER INFORMATION: 3' PCR primer for SEQ ID NO:7

<400> SEQUENCE: 9
ggcaagagca tgaattaaat ctgtg                                           25

<210> SEQ ID NO 10
<211> LENGTH: 41
<212> TYPE: DNA
<213> ORGANISM: Escherichia coli
```

-continued

```
<220> FEATURE:
<221> NAME/KEY: misc_feature
<222> LOCATION: (13)..(41)
<223> OTHER INFORMATION: 5' pCR primer for SEQ ID NO:7

<400> SEQUENCE: 10
ggcggcggcg gctattaaga gattgcaaag acattaaggg t                    41

<210> SEQ ID NO 11
<211> LENGTH: 34
<212> TYPE: DNA
<213> ORGANISM: Escherichia coli
<220> FEATURE:
<221> NAME/KEY: misc_feature
<222> LOCATION: (10)..(34)
<223> OTHER INFORMATION: 3' PCR primer for SEQ ID NO:7

<400> SEQUENCE: 11
ggcggcggcg gcaagagcat gaattaaatc tgtg                            34

<210> SEQ ID NO 12
<211> LENGTH: 151
<212> TYPE: DNA
<213> ORGANISM: Escherichia coli
<220> FEATURE:
<221> NAME/KEY: misc_feature
<222> LOCATION: (1)..(150)
<223> OTHER INFORMATION: specific for serotype O157:H7

<400> SEQUENCE: 12
aaaagttgcc gtttgcgtag aatgtagaca aaagcgtggt gtcaaggagg ggaggttaac    60
gtcatagtga agaggagtgg tggcaccgat caggtcatga tgtagtggaa gtgcctggag   120
gtgagcaggc agggcaagat tacgaaagcc c                                 151

<210> SEQ ID NO 13
<211> LENGTH: 27
<212> TYPE: DNA
<213> ORGANISM: Escherichia coli
<220> FEATURE:
<221> NAME/KEY: misc_feature
<222> LOCATION: (1)..(27)
<223> OTHER INFORMATION: 5' PCR primer for SEQ ID NO:12

<400> SEQUENCE: 13
aaaagttgcc gtttgcgtag aatgtag                                    27

<210> SEQ ID NO 14
<211> LENGTH: 26
<212> TYPE: DNA
<213> ORGANISM: Escherichia coli
<220> FEATURE:
<221> NAME/KEY: misc_feature
<222> LOCATION: (1)..(25)
<223> OTHER INFORMATION: 3' PCR primer for SEQ ID NO:12

<400> SEQUENCE: 14
gggctttcgt aatcttgccc tgcctg                                     26

<210> SEQ ID NO 15
<211> LENGTH: 177
<212> TYPE: DNA
<213> ORGANISM: Escherichia coli
<220> FEATURE:
<221> NAME/KEY: misc_feature
<222> LOCATION: (1)..(190)
<223> OTHER INFORMATION: specific for serotype O157:H7

<400> SEQUENCE: 15
```

```
catatctcca gccgccagtg tcgatgtggc acttatctgt gaacttgatg aacaatggag        60
ttttgtcgaa aacaaagctc gtcagcagtg gcactggtac gcgtataaga ccaaagctga       120
cggtgtgctg gcttacactt ttggtcctcg cactgatgaa acatgccgtg agttgcc          177

<210> SEQ ID NO 16
<211> LENGTH: 24
<212> TYPE: DNA
<213> ORGANISM: Escherichia coli
<220> FEATURE:
<221> NAME/KEY: misc_feature
<222> LOCATION: (1)..(24)
<223> OTHER INFORMATION: 5' PCR primer for SEQ ID NO:15

<400> SEQUENCE: 16
catatctcca gccgccagtg tcga                                               24

<210> SEQ ID NO 17
<211> LENGTH: 26
<212> TYPE: DNA
<213> ORGANISM: Escherichia coli
<220> FEATURE:
<221> NAME/KEY: misc_feature
<222> LOCATION: (1)..(26)
<223> OTHER INFORMATION: 3' PCR primer for SEQ ID NO:15

<400> SEQUENCE: 17
gcttcaggaa ttccggcaac tcacgg                                             26
```

DNA SEQUENCES FOR THE DETECTION OF AND DIFFERENTIATION AMONGST PATHOGENIC E. COLI

FIELD OF INVENTION

The field of invention relates to a rapid method for detection of and differentiation amongst *Escherichia coli* bacteria based on the presence of nucleic acid sequences, in particular, to a PCR-based method for detection, and to oligonucleotide molecules and reagents and kits useful therefore.

BACKGROUND OF INVENTION

*Escherichia coli* (*E. coli*) is a gram-negative rod-shaped bacterium. Although most strains of *E. coli* are benign and are found as normal intestinal flora of humans and other animals, some strains are pathogenic and can lead to sometimes-fatal disease. Different strains of pathogenic *E. coli* differ in their epidemiology, clinical course and potential for causing outbreaks of disease. Passage of disease is generally through the fecal/oral route.

Pathogenicity has been linked to several serotypes, as defined by O and H antigens. Different pathogenic serotypes are associated with different clinical disease courses and have associated with them different levels of concern from the standpoint of public health. Several outbreaks of disease have been tracked to food and water borne sources of pathogenic *E. coli*.

One serotype in particular, serotype *E. coli* O157:H7, has been associated with several food and water borne outbreaks and is regulated as an adulterant in ground beef by the USDA with a zero tolerance standard.

Since *E. coli* is ubiquitous, and most serotypes are non-pathogenic, the ability to detect pathogenic serotypes, and to differentiate among pathogenic serotypes with different clinical and public health implications is useful.

It is desirable, therefore, to have a test for the rapid detection of pathogenic *E. coli* and to differentiate those of greater public health and regulatory concern.

SUMMARY OF INVENTION

The present invention includes:

A method for detecting the presence of pathogenic *E. coli* in a sample comprising (a) performing PCR amplification of the sample using a primer pair selected from the group consisting of (i) SEQ ID NOs:2 and 3, (ii) SEQ ID NOs:5 and 6, (iii) SEQ ID NOs:8 and 9, (iv) SEQ ID NOs:10 and 11, (v) SEQ ID NOs:13 and 14, and (vi) SEQ ID NOs:16 and 17, to produce a PCR amplification result; and (b) examining the PCR amplification result of step (a) to detect for an amplification product of the primer pair, whereby a positive detection of the amplification product of the primer pair indicates the presence of pathogenic *E. coli* in the sample. Preferably, the primer pair is selected from the group consisting of (a)(ii), (a)(iii), and (a)(iv).

A method for detecting the presence of pathogenic *E. coli* in a sample, the method comprising: (a) performing PCR amplification of the sample using two different primer pairs selected from the group consisting of (i) SEQ ID NOs:2 and 3, (ii) SEQ ID NOs:5 and 6, (iii) SEQ ID NOs:8 and 9, (iv) SEQ ID NOs:10 and 11, (v) SEQ ID NOs:13 and 14, and (vi) SEQ ID NOs:16 and 17, to produce a PCR amplification result; and (b) examining the PCR amplification result of step (a) to detect for amplification products of both of the two different primer pairs, whereby a positive detection of the amplification products of both of the two different primer pairs indicates the presence of pathogenic *E. coli* in the sample. The two different primer pairs comprise preferably (a)(ii) and (a)(iii), even more preferably (a)(ii) and (a)(iv).

Any of the above methods, wherein in step (b) a melting curve analysis is used to detect for amplification product.

Any of the above methods, further comprising a step of preparing the sample for PCR amplification prior to said step (a). Preferably, the preparing step comprises at least one of the following processes: (1) bacterial enrichment, (2) separation of bacterial cells from the sample, (3) cell lysis, and (4) total DNA extraction.

Any of the above methods, wherein the sample comprises a food sample, a water sample, or a selectively enriched food matrix.

An isolated polynucleotide for detection of pathogenic *E. coli* comprising SEQ ID NO:2, SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:16, or SEQ ID NO:17.

A kit for detection of pathogenic *E. coli*, comprising (a) at least one primer pair selected from the group consisting of (i) SEQ ID NOs:2 and 3, (ii) SEQ ID NOs:5 and 6, (iii) SEQ ID NOs:8 and 9, (iv) SEQ ID NOs:10 and 11, (v) SEQ ID NOs:13 and 14, and (vi) SEQ ID NOs:16 and 17; and (b) thermostable DNA polymerase. The kit comprises preferably both (a)(ii) and (a)(iii), even more preferably, both (a)(ii) and (a)(iv).

A replication composition for use in performance of PCR, comprising at least one primer pair selected from the group consisting of (i) SEQ ID NOs:2 and 3, (ii) SEQ ID NOs:5 and 6, (iii) SEQ ID NOs:8 and 9, (iv) SEQ ID NOs:10 and 11, (v) SEQ ID NOs:13 and 14, and (vi) SEQ ID NOs:16 and 17; and (b) thermostable DNA polymerase. The replication composition comprises preferably both (a)(ii) and (a)(iii), even more preferably, both (a)(ii) and (a)(iv).

A tablet comprising any of the above replication compositions, and a kit for detection of pathogenic *E. coli* in a sample, comprising the tablet.

SUMMARY OF THE SEQUENCES

SEQ ID NO:1 is the nucleotide sequence of pathogenic *E. coli* the detection of which specifically shows the presence of pathogenic *E. coli* of serotypes O157:H7, O157:HNM, O55:H7, O26:H11, or O145:HNM. SEQ ID NO:1 is bounded by, contains, and is amplified by the primers SEQ ID NO:2 and SEQ ID NO:3.

SEQ ID NO:2 is the nucleotide sequence of a 5' primer to a region of the genome of pathogenic *E. coli* that will specifically amplify DNA of pathogenic *E. coli* of serotypes O157:H7, O157:HNM, O55:H7, O26:H11, or O145:HNM in a polymerase chain reaction with bacterial DNA and SEQ ID NO:3.

SEQ ID NO:3 is the nucleotide sequence of a 3' primer to a region of the genome of pathogenic *E. coli* that will specifically amplify DNA of pathogenic *E. coli* of serotypes O157:H7, O157:HNM, O55:H7, O26:H11, or O145:HNM in a polymerase chain reaction with bacterial DNA and SEQ ID NO:2.

SEQ ID NO:4 is the nucleotide sequence of pathogenic *E. coli* the detection of which specifically shows the presence of pathogenic *E. coli* of serotypes O157:H7, O157:HNM. O55:H7, O26:H11, O26:HNM, O145:HNM, or O111:HNM. SEQ ID NO:4 is bounded by, contains, and is amplified by the use of primers SEQ ID NO:5 and SEQ ID NO:6.

SEQ ID NO 5 is the nucleotide sequence of a 5' primer to a region of the genome of pathogenic *E. coli* that will specifically amplify DNA of pathogenic *E. coli* of serotypes O157: H7, O157:HNM. O55:H7, O26:H11, O26:HNM, O145: HNM, or O111:HNM in a polymerase chain reaction with bacterial DNA and SEQ ID NO:6.

SEQ ID NO:6 is the nucleotide sequence of a 3' primer to a region of the genome of pathogenic *E. coli* that will specifically amplify DNA of pathogenic *E. coli* of serotypes O157: H7, O157:HNM. O55:H7, O26:H11, O26:HNM, O145: HNM, or O111:HNM in a polymerase chain reaction with bacterial DNA and SEQ ID NO:5.

SEQ ID NO:7 is the nucleotide sequence of pathogenic *E. coli* the detection of which specifically shows the presence of pathogenic *E. coli* of serotypes O157:H7, O157:HNM or O55:H7. SEQ ID NO:7 is bounded by, contains, and is amplified by the use of primers SEQ ID NO:8 and SEQ ID NO:9. SEQ ID NO:5 is also amplified by the use of primers represented by SEQ ID NO:10 and SEQ ID NO:11, which are modifications of SEQ ID NO:8 and SEQ ID NO:9, respectively.

SEQ ID NO:8 is the nucleotide sequence of a 5' primer to a region of the genome of pathogenic *E. coli* that will specifically amplify DNA of pathogenic *E. coli* of serotypes O157: H7, O157:HNM or O55:H7 in a polymerase chain reaction with bacterial DNA and SEQ ID NO:9.

SEQ ID NO: 9 is the nucleotide sequence of a 3' primer to a region of the genome of pathogenic *E. coli* that will specifically amplify DNA of pathogenic *E. coli* of serotypes O157: H7, O157:HNM or O55:H7 in a polymerase chain reaction with bacterial DNA and SEQ ID NO:8.

SEQ ID NO:10 is a modification of SEQ ID NO:8. SEQ ID NO:10 includes the entire sequence of SEQ ID NO:8 to which has been added a GC rich clamp. Addition of this clamp does not alter the target specificity, but does alter the melting temperature of the amplified product. SEQ ID NO:10 is the nucleotide sequence of a 5' primer to a region of the genome of pathogenic *E. coli* that will specifically amplify DNA of pathogenic *E. coli* of serotypes O157:H7, O157:HNM or O55:H7 in a polymerase chain reaction with bacterial DNA and SEQ ID NO:11.

SEQ ID NO:11 is a modification of SEQ ID NO:9. SEQ ID NO:11 includes the entire sequence of SEQ ID NO:9 to which has been added a GC rich clamp. Addition of this clamp does not alter the target specificity, but does alter the melting temperature of the amplified product. SEQ ID NO:11 is the nucleotide sequence of a 3' primer to a region of the genome of pathogenic *E. coli* that will specifically amplify DNA of pathogenic *E. coli* of serotypes O157:H7, O157:HNM or O55:H7 in a polymerase chain reaction with bacterial DNA and SEQ ID NO:10.

SEQ ID NO:12 is the nucleotide sequence of pathogenic *E. coli* the detection of which specifically shows the presence of pathogenic *E. coli* serotypes including O157:H7. SEQ ID NO:12 is bounded by, contains, and is amplified by the primers SEQ ID NO:13 and SEQ ID NO:14.

SEQ ID NO:13 is the nucleotide sequence of a 5' primer to a region of the genome of pathogenic *E. coli* that will specifically amplify DNA of pathogenic *E. coli* of serotypes including O157:H7 in a polymerase chain reaction with bacterial DNA and SEQ ID NO:14.

SEQ ID NO:14 is the nucleotide sequence of a 3' primer to a region of the genome of pathogenic *E. coli* that will specifically amplify DNA of pathogenic *E. coli* of serotypes including O157:H7 in a polymerase chain reaction with bacterial DNA and SEQ ID NO:13.

SEQ ID NO:15 is the nucleotide sequence of pathogenic *E. coli* the detection of which specifically shows the presence of pathogenic *E. coli* of serotypes including O157:H7. SEQ ID NO:15 is bounded by, contains, and is amplified by the primers SEQ ID NO:16 and SEQ ID NO:17.

SEQ ID NO:16 is the nucleotide sequence of a 5' primer to a region of the genome of pathogenic *E. coli* that will specifically amplify DNA of pathogenic *E. coli* of serotypes including O157:H7 in a polymerase chain reaction with bacterial DNA and SEQ ID NO:17.

SEQ ID NO:17 is the nucleotide sequence of a 3' primer to a region of the genome of pathogenic *E. coli* that will specifically amplify DNA of pathogenic *E. coli* of serotypes including O157:H7 in a polymerase chain reaction with bacterial DNA and SEQ ID NO:16.

The sequences conform with 37 C.F.R. §§1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

DETAILED DESCRIPTION OF PREFERRED EMBODIMENTS

Figure 1:
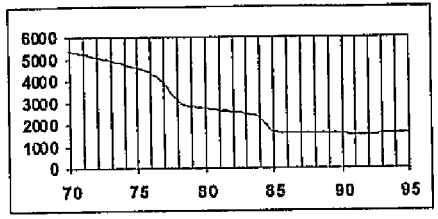
FIG. 1 shows the process of melting curve analysis. The change in fluorescence of the target DNA is captured during melting. Mathematical analysis of the negative of the change of the log of fluorescence divided by the change in temperature plotted against the temperature results in the graphical peak known as a melting curve.
Figure 1:
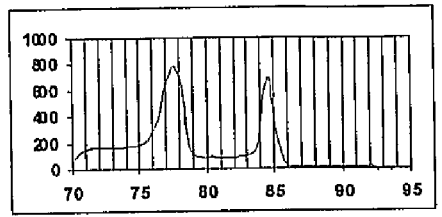

The disclosure of each reference set forth herein is incorporated by reference in its entirety.

Definitions

In this disclosure, a number of terms and abbreviations are used. The following definitions are provided.

"Polymerase chain reaction" is abbreviated PCR.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "polynucleotide", "polynucleotide sequence", "nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more strands of cDNA, genomic DNA, synthetic DNA, or mixtures thereof.

The term "amplification product" refers to nucleic acid fragments produced during a primer-directed amplification reaction. Typical methods of primer-directed amplification include polymerase chain reaction (PCR), ligase chain reaction (LCR) or strand displacement amplification (SDA). If PCR methodology is selected, the replication composition may comprise the components for nucleic acid replication, for example: nucleotide triphosphates, two (or more) primers with appropriate sequences, thermostable polymerase, buffers, solutes and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions may comprise, for example: a thermostable ligase (e.g., *T. aquaticus* ligase), two sets of adjacent oligonucleotides (wherein one member of each set is complementary to each of the target strands), Tris-HCl buffer, KCl, EDTA, NAD, dithiothreitol and salmon sperm DNA. See, for example, Tabor et al., *Proc. Acad. Sci. U.S.A.,* 82:1074-1078 (1985)).

The term "primer" refers to an oligonucleotide (synthetic or occurring naturally), which is capable of acting as a point of initiation of nucleic acid synthesis or replication along a complementary strand when placed under conditions in which synthesis of a complementary stand is catalyzed by a polymerase.

The term "probe" refers to an oligonucleotide (synthetic or occurring naturally) that is complementary (though not necessarily fully complementary) to a polynucleotide of interest and forms a duplexed structure by hybridization with at least one strand of the polynucleotide of interest.

The term "replication inhibitor moiety" refers to any atom, molecule or chemical group that is attached to the 3' terminal hydroxyl group of an oligonucleotide that will block the initiation of chain extension for replication of a nucleic acid strand. Examples include, but are not limited to: 3'-deoxynucleotides (e.g., cordycepin), dideoxynucleotides, phosphate, ligands (e.g., biotin and dinitrophenol), reporter molecules (e.g., fluorescein and rhodamine), carbon chains (e.g., propanol), a mismatched nucleotide or polynucleotide, or peptide nucleic acid units. The term "non-participatory" will refer to the lack of participation of a probe or primer in a reaction for the amplification of a nucleic acid molecule. Specifically a non-participatory probe or primer is one that will not serve as a substrate for, or be extended by, a DNA or RNA polymerase. A "non-participatory probe" is inherently incapable of being chain extended by a polymerase. It may or may not have a replication inhibitor moiety.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one preferred embodiment the length for a hybridizable nucleic acid is at least about 10 nucleotides. More preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

"Gene" refers to a nucleic acid fragment that expresses a specific protein, including regulatory sequences preceding (5' non-coding sequences) and following (3' non-coding sequences) the coding sequence.

The term "expression", as used herein, refers to the transcription and stable accumulation of sense (mRNA) or antisense RNA derived from the nucleic acid fragment of the invention. Expression may also refer to translation of mRNA into a polypeptide.

Standard recombinant DNA and molecular cloning techniques used here are well known in the art and are described by Sambrook, J., Fritsch, E. F. and Maniatis, T., *Molecular Cloning: A Laboratory Manual,* $2^{nd}$ ed., Cold Spring Harbor Laboratory: Cold Spring Harbor, N.Y. (1989) (hereinafter "Maniatis"); and by Ausubel, F. M. et al., *Current Protocols in Molecular Biology,* published by Greene Publishing Assoc. and Wiley-Interscience (1987).

Primers/Oligonucleotides

Oligonucleotides of the instant invention have been developed for the detection and identification of pathogenic *E. coli*.

Oligonucleotides of the instant invention are set forth in SEQ ID NOs:1-17.

Certain oligonucleotides of the instant invention may be used as primers for polymerase chain reaction (PCR) amplification, as shown below in Table I.

TABLE I

| Primer Set | SEQ ID NOs |
|---|---|
| PS1 | 2 and 3 |
| PS2 | 5 and 6 |
| PS3 | 8 and 9 |
| PS4 | 10 and 11 |
| PS5 | 13 and 14 |
| PS6 | 16 and 17 |

The primer sets PS1 (SEQ ID NO:2 and SEQ ID NO:3), PS2 (SEQ ID NO:5 and SEQ ID NO:6), PS3 (SEQ ID NO:8 and SEQ ID NO:9), PS5 (SEQ ID NO:13 and SEQ ID NO:14), and PS6 (SEQ ID NO:16 and SEQ ID NO:17) were designed based on sequence analysis of a region of the E. coli O157:H7 genome. The primer set PS4 (SEQ ID NO:10 and SEQ ID NO:11) were modifications of the primers in PS3 that were generated to raise the melting point of the PCR product without altering the specificity of the primers. Blast searches of the NCBI database revealed no significant sequence homologies to genes of known function. Primer design was not aided by any software program.

These oligonucleotide primers may also be useful for other nucleic acid amplification methods such as the ligase chain reaction (LCR) (Backman et al., 1989, EP 0 320 308; Carrino et al., 1995, *J. Microbiol. Methods* 23: 3-20); nucleic acid sequence-based amplification (NASBA), (Carrino et al., 1995, supra); and self-sustained sequence replication (3SR) and 'Q replicase amplification' (Pfeffer et al., 1995 *Veterinary Res. Comm.,* 19: 375-407).

Oligonucleotides of the instant invention also may be used as hybridization probes. Hybridization using DNA probes has been frequently used for the detection of pathogens in food, clinical and environmental samples, and the methodology are generally known to one skilled in the art. It is generally recognized that the degree of sensitivity and specificity of probe hybridization is lower than that achieved through the previously described amplification techniques.

Assay Methods

SEQ ID NOs:1-17 may be used in a variety of formats for the detection of pathogenic *E. coli*. Most preferred are primer-directed amplification methods and nucleic acid hybridization methods.

These methods may be used to detect pathogenic *E. coli* in a sample, e.g., from an animal, environmental or food source suspected of contamination.

Both amplification-based and hybridization-based methods using the nucleic acid sequences and oligonucleotides of the invention also may be used to confirm the identification of *E. coli* in a complex matrix or purified culture. A preferred embodiment of the instant invention comprises (1) culturing a complex sample mixture in a non-selective growth media to resuscitate the target bacteria, (2) releasing total target bacterial DNA, and (3) subjecting the total DNA to amplification protocol with a primer pair of the invention.

Primer-Directed Amplification Assay Methods

In one preferred embodiment, primer pairs PS1-PS6 may be used as primers for use in primer-directed nucleic acid amplification for the detection of pathogenic *E. coli*.

A variety of primer-directed nucleic acid amplification methods are known in the art including thermal cycling methods (e.g., PCR, RT-PCR, and LCR), as well as isothermal methods and strand displacement amplification (SDA).

The preferred method is PCR.

Sample Preparation

The oligonucleotides and methods according to the instant invention may be used directly with any suitable clinical or environmental samples, without any need for sample preparation. In order to achieve higher sensitivity, and in situations where time is not a limiting factor, it is preferred that the samples be pre-treated, and that pre-amplification enrichment is performed.

The minimum industry standard for the detection of foodborne bacterial pathogens is a method that will reliably detect the presence of one pathogen cell in 25 g of food matrix as described in Andrews et al., 1984, "Food Sample and Preparation of Sample Homogenate", Chapter 1 in *Bacteriological Analytical Manual,* 8th Edition, Revision A, Association of Official Analytical Chemists, Arlington, Va. In order to satisfy this stringent criterion, enrichment methods and media have been developed to enhance the growth of the target pathogen cell in order to facilitate its detection by biochemical, immunological or nucleic acid hybridization means. Typical enrichment procedures employ media that will enhance the growth and health of the target bacteria and also inhibit the growth of any background or non-target microorganisms present. For example, the U.S. Department of Agriculture (USDA) has set forth a protocol for enrichment of samples of ground beef to be tested for pathogenic *E. coli*. U.S. Food and Drug Administration, Bacterial Analytical Manual.

Selective media have been developed for a variety of bacterial pathogens and one of skill in the art will know to select a medium appropriate for the particular organism to be enriched. A general discussion and recipes of non-selective media are described in the FDA Bacteriological Analytical Manual. (1998) published and distributed by the Association of Analytical Chemists, Suite 400, 2200 Wilson Blvd, Arlington, Va. 22201-3301.

After selective growth, a sample of the complex mixtures is removed for further analysis. This sampling procedure may be accomplished by a variety of means well known to those skilled in the art. In a preferred embodiment, 5 µl of the enrichment culture is removed and added to 200 µl of lysis solution containing protease. The lysis solution is heated at 37° C. for 20 min followed by protease inactivation at 95° C. for 10 min as described in the BAX® System User's Guide, Qualicon, Inc., Wilmington, Del.

PCR Assay Methods

A preferred method for detecting the presence of pathogenic *E. coli* in a sample comprises (a) performing PCR amplification of the sample using a primer pair selected from the group consisting of PS1, PS2, PS3, PS4, PS5, and PS6, to produce a PCR amplification result; and (b) examining the PCR amplification result of step (a) to detect for an amplification product of the primer pair, whereby a positive detection of the amplification product of the primer pair indicates the presence of pathogenic *E. coli* in the sample.

More preferably, in the foregoing method, the primer pair is selected from the group consisting of PS2, PS3, and PS4.

Another preferred method for detecting the presence of pathogenic *E. coli* in a sample comprises (a) performing PCR amplification of the sample using two different primer pairs selected from the group consisting of PS1, PS2, PS3, PS4, PS5, and PS6, to produce a PCR amplification result; and (b) examining the PCR amplification result of step (a) to detect for amplification products of both of the two different primer pairs, whereby a positive detection of the amplification products of both of the two different primer pairs indicates the presence of pathogenic *E. coli* in the sample.

In the foregoing method, the two primer pairs preferably comprise PS2 and PS3, more preferably, PS2 and PS4.

In another preferred embodiment, prior to performing PCR amplification, a step of preparing the sample may be carried out. The preparing step may comprise at least one of the following processes: (1) bacterial enrichment, (2) separation of bacterial cells from the sample, (3) cell lysis, and (4) total DNA extraction.

Amplification Conditions

A skilled person will understand that any generally acceptable PCR conditions may be used for successfully detecting the target pathogenic E. coli bacteria using the oligonucleotides of the instant invention, and depending on the sample to be tested and other laboratory conditions, routine optimization for the PCR conditions may be necessary to achieve optimal sensitivity and specificity. Optimally, they achieve PCR amplification products from all of the intended specific targets while giving no PCR product for other, non-target species.

In a preferred embodiment, the following reagents and cycling conditions may be used. Forty-five microliters of lysate added to a PCR tube containing one BAX® reagent tablet (manufactured by Qualicon, Inc., Wilmington, Del.), the tablet containing Taq DNA polymerase, deoxynucleotides, SYBR® Green (Molecular Probes, Eugene, Oreg.), and buffer components, and 5 microliters of primer mix, to achieve a final concentration in the PCR of 0.150 micromoles for each primer. Preferred PCR cycling conditions: 94° C., 2 min initial DNA denaturation, followed by 38 cycles of 94° C., 15 seconds and annealing/extension at 70° C. for 3 minutes.

Detection/Examination/Analysis

Primer-directed amplification products can be analyzed using various methods.

Homogenous detection refers to a preferred method for the detection of amplification products where no separation (such as by gel electrophoresis) of amplification products from template or primers is necessary. Homogeneous detection is typically accomplished by measuring the level of fluorescence of the reaction mixture in the presence of a fluorescent dye.

In a preferred embodiment, DNA melting curve analysis is used to carry out homogenous detection, particularly with the BAX® System hardware and reagent tablets from Qualicon Inc. The details of the system are given in U.S. Pat. No. 6,312,930 and PCT Publication Nos. WO 97/11197 and WO 00/66777, each of which is hereby incorporated by reference in its entirety.

Melting curve analysis detects and quantifies double stranded nucleic acid molecule ("dsDNA" or "target") by monitoring the fluorescence of the target amplification product ("target amplicon") during each amplification cycle at selected time points.

As is well known to the skilled artisan, the two strands of a dsDNA separate or melt, when the temperature is higher than its melting temperature. Melting of a dsDNA molecule is a process, and under a given solution condition, melting starts at a temperature (designated $T_{MS}$ hereinafter), and completes at another temperature (designated $T_{ME}$ hereinafter). The familiar term, $T_m$, designates the temperature at which melting is 50% complete.

A typical PCR cycle involves a denaturing phase where the target dsDNA is melted, a primer annealing phase where the temperature optimal for the primers to bind to the now-single-stranded target, and a chain elongation phase (at a temperature $T_E$) where the temperature is optimal for DNA polymerase to function.

According to the present invention, $T_{MS}$ should be higher than $T_E$, and $T_{ME}$ should be lower (often substantially lower) than the temperature at which the DNA polymerase is heat-inactivated. Melting characteristics are effected by the intrinsic properties of a given dsDNA molecule, such as deoxynucleotide composition and the length of the dsDNA.

Intercalating dyes will bind to double stranded DNA. The dye/dsDNA complex will fluoresce when exposed to the appropriate excitation wavelength of light, which is dye dependent, and the intensity of the fluorescence may be proportionate to concentration of the dsDNA. Methods taking advantage of the use of DNA intercalating dyes to detect and quantify dsDNA are known in the art. Many dyes are known and used in the art for these purposes. The instant methods also take advantage of such relationship.

An example of such dyes includes intercalating dyes. Examples of such dyes include, but are not limited to, SYBR Green-I®, ethidium bromide, propidium iodide, TOTO®)-1 {Quinolinium, 1-1'-[1,3-propanediylbis[(dimethyliminio)-3, 1-propanediyl]]bis[4-[(3-methyl-2(3H)-benzothiaz-olylidene)methyl]]-, tetraiodide}, and YoPro® {Quinolinium, 4-[(3-methyl-2(3H)-benzoxazolylidene)methyl]-1-[3-(trimethylammonio)propyl]-,diiodide}. Most preferred for the instant invention is a non-asymmetrical cyanide dye such as SYBR Green-I®, manufactured by Molecular Probes, Inc. (Eugene, Oreg.).

Melting curve analysis is achieved by monitoring the change in fluorescence while the temperature is increased. When the temperature reaches the $T_{MS}$ specific for the target amplicon, the dsDNA begins to denature. When the dsDNA denatures, the intercalating dye dissociates from the DNA and fluorescence decreases. Mathematical analysis of the negative of the change of the log of fluorescence divided by the change in temperature plotted against the temperature results in the graphical peak known as a melting curve.

The data transformation process shown in FIG. 1 involves the following:
1. Interpolate data to get evenly spaced data points
2. Take a log of the fluorescence (F)
3. Smooth log F
4. Calculate –d(log F)/dT
5. Reduce data to 11-13 data points spaced one degree apart (depending on the target organism).

The instant homogenous detection method can be used to detect and quantify target dsDNAs, from which the presence and level of target organisms can be determined. This method is very specific and sensitive. The fewest number of target dsDNA detectable is between one and 10 under typical reaction conditions and volumes.

Homogenous detection may be employed to carry out "real-time" primer-directed nucleic acid amplifications, using primer pairs of the instant invention (e.g., "real-time" PCR and "real-time" RT-PCR). Preferred "real-time" methods are set forth in U.S. Pat. Nos. 6,171,785 and 5,994,056, each of which is hereby incorporated by reference in its entirety.

Another detection method is the 5' nuclease detection method, as set forth in U.S. Pat. Nos. 5,804,375, 5,538,848, 5,487,972, and 5,210,015, each of which is hereby incorporated by reference in its entirety.

A variety of other PCR detection methods are known in the art including standard non-denaturing gel electrophoresis (e.g., acrylamide or agarose), denaturing gradient gel electrophoresis, and temperature gradient gel electrophoresis. Standard non-denaturing gel electrophoresis is a simple and quick method of PCR detection, but may not be suitable for all applications.

Denaturing Gradient Gel Electrophoresis (DGGE) is a separation method that detects differences in the denaturing behavior of small DNA fragments (200-700 bp). The principle of the separation is based on both fragment length and nucleotide sequence. In fragments that are the same length, a difference as little as one base pair can be detected. This is in contrast to non-denaturing gel electrophoresis, where DNA fragments are separated only by size. This limitation of non-denaturing gel electrophoresis results because the difference in charge density between DNA molecules is near neutral and plays little role in their separation. As the size of the DNA fragment increases, its velocity through the gel decreases.

DGGE is primarily used to separate DNA fragments of the same size based on their denaturing profiles and sequence. Using DGGE, two strands of a DNA molecule separate, or melt, when heat or a chemical denaturant is applied. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking". Consequently, a DNA molecule may have several melting domains with each of their individual characteristic denaturing conditions determined by their nucleotide sequence. DGGE exploits the fact that otherwise identical DNA molecules having the same length and DNA sequence, with the exception of only one nucleotide within a specific denaturing domain, will denature at different temperatures or Tm. Thus, when the double-stranded (ds) DNA fragment is electrophoresed through a gradient of increasing chemical denaturant it begins to denature and undergoes both a conformational and mobility change. The dsDNA fragment will travel faster than a denatured single-stranded (ss) DNA fragment, since the branched structure of the single-stranded moiety of the molecule becomes entangled in the gel matrix. As the denaturing environment increases, the ds DNA fragment will completely dissociate and mobility of the molecule through the gel is retarded at the denaturant concentration at which the particular low denaturing domains of the DNA strand dissociate. In practice, the electrophoresis is conducted at a constant temperature (around 60° C.) and chemical denaturants are used at concentrations that will result in 100% of the DNA molecules being denatured (i.e., 40% formamide and 7M urea). This variable denaturing gradient is created using a gradient maker, such that the composition of each DGGE gel gradually changes from 0% denaturant up to 100% denaturant. Of course, gradients containing a reduced range of denaturant (e.g., 35% to 60%) may also be poured for increased separation of DNA.

The principle used in DGGE can also be applied to a second method that uses a temperature gradient instead of a chemical denaturant gradient. This method is known as Temperature Gradient Gel Electrophoresis (TGGE). This method makes use of a temperature gradient to induce the conformational change of dsDNA to ssDNA to separate fragments of equal size with different sequences. As in DGGE, DNA fragments with different nucleotide sequences will become immobile at different positions in the gel. Variations in primer design can be used to advantage in increasing the usefulness of DGGE for characterization and identification of the PCR products. These methods and principles of using primer design variations are described in PCR Technology Principles and Applications, Henry A. Erlich Ed., M. Stockton Press, NY, pages 71 to 88 (1988).

Instrumentation

According to a preferred embodiment, the BAX® System (DuPont Qualicon, Wilmington, Del.) and melting curve analysis are used.

Reagents and Kits

Any suitable nucleic acid replication composition ("replication composition") in any format can be used.

A typical replication composition for PCR amplification may comprise, for example, dATP, dCTP, dGTP, dTTP, target specific primers and a suitable polymerase.

If the replication composition is in liquid form, suitable buffers known in the art may be used (Sambrook, J. et al. 1989, Molecular Cloning: A Laboratory Manual, Second Edition, Cold Spring Harbor Laboratory Press).

Alternatively, if the replication composition is contained in a tablet form, then typical tabletization reagents may be included such as stabilizers and binding agents. Preferred tabletization technology is set forth in U.S. Pat. Nos. 4,762,857 and 4,678,812, each of which is hereby incorporated by reference in its entirety.

A preferred replication composition of the instant invention comprises (a) at least one primer pair selected from the group consisting of PS1, PS2, PS3, PS4, PS5, and PS6; and (b) thermostable DNA polymerase. More preferably, the replication composition comprises both primer pairs PS2 and PS3, even more preferably, both primer pairs PS2 and PS4.

A preferred kit of the instant invention comprises (a) at least one primer pair selected from the group consisting of PS1, PS2, PS3, PS4, PS5, and PS6; and (b) thermostable DNA polymerase. More preferably, the preferred kit comprises both primer pairs PS2 and PS3, even more preferably, both primer pairs PS2 and PS4.

A preferred tablet of the instant invention comprises (a) at least one primer pair selected from the group consisting of PS1, PS2, PS3, PS4, PS5, and PS6; and (b) thermostable DNA polymerase. More preferably, the preferred tablet comprises both primer pairs PS2 and PS3, even more preferably, both primer pairs PS2 and PS4. Even more preferably, a kit of the instant invention comprises the foregoing preferred tablet.

In another preferred embodiment, a replication composition contains an internal positive control. The advantages of an internal positive control contained within a PCR reaction have been previously described (U.S. Pat. No. 6,312,930 and PCT Application No. WO 97/11197, each of which is hereby incorporated by reference in its entirety, and include: (i) the control may be amplified using a single primer; (ii) the amount of the control amplification product is independent of any target DNA or RNA contained in the sample; (iii) the control DNA can be tabletted with other amplification reagents for ease of use and high degree of reproducibility in both manual and automated test procedures; (iv) the control can be used with homogeneous detection, i.e., without separation of product DNA from reactants; and (v) the internal control has a melting profile that is distinct from other potential amplification products in the reaction Control DNA will be of appropriate size and base composition to permit amplification in a primer-directed amplification reaction. The control DNA sequence may be obtained from the E. coli genome, or from another source, but must be reproducibly amplified under the same conditions that permit the amplification of the target amplification product.

The control reaction is useful to validate the amplification reaction. Amplification of the control DNA occurs within the same reaction tube as the sample that is being tested, and therefore indicates a successful amplification reaction when samples are target negative, i.e. no target amplification product is produced. In order to achieve significant validation of the amplification reaction a suitable number of copies of the control DNA must be included in each amplification reaction.

In some instances it may be useful to include an additional negative control replication composition. The negative control replication composition will contain the same reagents as the replication composition but without the polymerase. The primary function of such a control is to monitor spurious background fluorescence in a homogeneous format when the method employs a fluorescent means of detection.

Replication compositions may be modified depending on whether they are designed to be used to amplify target DNA or the control DNA. Replication compositions that will amplify the target DNA (test replication compositions) may include (i) a polymerase (generally thermostable), (ii) a primer pair capable of hybridizing to the target DNA and (iii) necessary buffers for the amplification reaction to proceed. Replication compositions that will amplify the control DNA (positive control, or positive replication composition) may include (i) a polymerase (generally thermostable) (ii) the control DNA; (iii) at least one primer capable of hybridizing to the control DNA; and (iv) necessary buffers for the amplification reaction to proceed.

Nucleic Acid Hybridization Methods

Probes particularly useful in nucleic acid hybridization methods are any of SEQ ID NOs: 1-17 or sequences derived therefrom.

The basic components of a nucleic acid hybridization test include a probe, a sample suspected of containing pathogenic *E. coli*, and a specific hybridization method. Probes are single stranded nucleic acid sequences which are complementary to the nucleic acid sequences to be detected. Probes are "hybridizable" to the nucleic acid sequence to be detected. Typically the probe length can vary from as few as 5 bases to the full length of the *E. coli* diagnostic sequence and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base. A probe may be composed of either RNA or DNA. The form of the nucleic acid probe may be a marked single stranded molecule of just one polarity or a marked single stranded molecule having both polarities present. The form of the probe, like its length, will be determined by the type of hybridization test to be done.

The sample may or may not contain pathogenic *E. coli*. The sample may take a variety of forms, however will generally be extracted from an animal, environmental or food source suspected of contamination.

The DNA may be detected directly but most preferably, the sample nucleic acid must be made available to contact the probe before any hybridization of probe and target molecule can occur. Thus the organism's DNA must be free from the cell and placed under the proper conditions before hybridization can occur. Methods of in solution hybridization necessitate the purification of the DNA in order to be able to obtain hybridization of the sample DNA with the probe. This has meant that utilization of the in solution method for detection of target sequences in a sample requires that the nucleic acids of the sample must first be purified to eliminate protein, lipids, and other cell components, and then contacted with the probe under hybridization conditions. Methods for the purification of the sample nucleic acid are common and well known in the art (Maniatis, supra).

Similarly, hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur.

The concentration of probe or target in the mixture will determine the time necessary for hybridization to occur. The higher the probe or target concentration, the shorter the hybridization incubation time needed.

In one preferred embodiment, hybridization assays may be conducted directly on cell lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to DNA at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30-50% (v/v).

Alternatively, one can purify the sample nucleic acids prior to probe hybridization. A variety of methods are known to one of skill in the art (e.g., phenol-chloroform extraction, Isoquick extraction (MicroProbe Corp., Bothell, Wash.), and others). Pre-hybridization purification is particularly useful for standard filter hybridization assays. Furthermore, purification facilitates measures to increase the assay sensitivity by incorporating in vitro RNA amplification methods such as self-sustained sequence replication (see for example Fahy et al., In *PCR Methods and Applications*, Cold Spring Harbor Laboratory: Cold Spring Harbor, N.Y. (1991), pp. 25-33) or reverse transcriptase PCR (Kawasaki, In *PCR Protocols: A Guide to Methods and Applications*, M. A. Innis et al., Eds., (1990), pp. 21-27).

Once the DNA is released, it can be detected by any of a variety of methods. However, the most useful embodiments have at least some characteristics of speed, convenience, sensitivity, and specificity.

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents which include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the DNA sequence.

The sandwich assay may be encompassed in an assay kit. This kit would include a first component for the collection of samples suspected of contamination and buffers for the disbursement and lysis of the sample. A second component would include media in either dry or liquid form for the hybridization of target and probe polynucleotides, as well as for the removal of undesirable and nonduplexed forms by washing. A third component includes a solid support (dipstick) upon which is fixed (or to which is conjugated) unlabeled nucleic acid probe(s) that is (are) complementary to a part of the E. coli genome. A fourth component would contain labeled probe that is complementary to a second and different region of the same DNA strand to which the immobilized, unlabeled nucleic acid probe of the third component is hybridized.

In another preferred embodiment, SEQ ID NOs:1-17 or derivations thereof may be used as 3' blocked detection probes in either a homogeneous or heterogeneous assay format. For example, a probe generated from these sequences may be 3' blocked or non-participatory and will not be extended by, or participate in, a nucleic acid amplification reaction. Additionally, the probe incorporates a label that can serve as a reactive ligand that acts as a point of attachment for the immobilization of the probe/analyte hybrid or as a reporter to produce detectable signal. Accordingly, genomic or cDNA isolated from a sample suspected of E. coli contamination is amplified by standard primer-directed amplification protocols in the presence of an excess of the 3' blocked detection probe to produce amplification products. Because the probe is 3' blocked, it does not participate or interfere with the amplification of the target. After the final amplification cycle, the detection probe anneals to the relevant portion of the amplified DNA and the annealed complex is then captured on a support through the reactive ligand.

In some instances it is desirable to incorporate a ligand labeled dNTP, with the label probe in the replication composition to facilitate immobilization of the PCR reaction product on a support and then detection of the immobilized product by means of the labeled probe reagent. For example a biotin, digoxigenin or digoxin labeled dNTP could be added to PCR reaction composition. The biotin or digoxin incorporated in the PCR product could then be immobilized respectively on to a strepavidin, anti-dixogin or antidigoxigenin antibody support. The immobilized PCR product could then be detected by the presence of the probe label.

Probes of the instant invention may be designed in several alternate forms. The 3' end of the probe is blocked from participating in a primer extension reaction by the attachment of a replication inhibiting moiety. Typical replication inhibitor moieties will include, but are not limited to: dideoxynucleotides, 3-deoxynucleotide, a sequence of mismatched nucleosides or nucleotides, 3' phosphate groups and chemical agents. Cordycepin (3' deoxyadenosine) is preferred.

The replication inhibitor is covalently attached to the 3' hydroxy group of the 3' terminal nucleotide of the non-participatory probe during chemical synthesis, using standard cyanoethyl phosphoramidite chemistry. This process uses solid phase synthesis chemistry in which the 3' end is covalently attached to an insoluble support (controlled pore glass, or "CPG") while the newly synthesized chain grows on the 5' terminus. 3-deoxyribonucleotides are the preferred replication inhibitors. Cordycepin (3-deoxyadenosine) is most preferred. Since the cordycepin will be attached to the 3' terminal end of the probe, the synthesis is initiated from a cordycepin covalently attached to CPG, 5-dimethoxytrityl-N-benzoyl-3-deoxyadenosine (cordycepin), 2-succinoyl-long chain alkylamino-CPG (Glen Research, Sterling, Va.).

The dimethoxytrityl group is removed and the initiation of the chain synthesis starts at the deprotected 5' hydroxyl group of the solid phase cordycepin. After the synthesis is complete, the oligonucleotide probe is cleaved off the solid support leaving a free 2' hydroxyl group on the 3'-terminally attached cordycepin. Other reagents can also be attached to the 3' terminus during the synthesis of the non-participatory probe to serve as replication inhibitors. These include, but are not limited to: other 3-deoxyribonucleotides, biotin, dinitrophenol, fluorescein, and digoxigenin. Each of these reagents are also derivatized on CPG supports (Glen Research; Clonetech Laboratories, Palo Alto, Calif.).

EXAMPLES

The present invention is further defined in the following Examples. It should be understood that these Examples, while indicating preferred embodiments of the invention, are given by way of illustration only.

General Methods and Materials Used in the Examples

Materials and Methods suitable for the maintenance and growth of bacterial cultures are well known in the art. Techniques suitable for use in the following Examples may be found in Manual of Methods for Genus Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in Biotechnology: A Textbook of Industrial Microbiology, Second Edition (1989) Sinauer Associates, Inc., Sunderland, Mass. or Bacteriological Analytical Manual. 6th Edition, Association of Official Analytical Chemists, Arlington, Va. (1984).

The medium used to grow the pathogenic E. coli strains and comparative non-target strains was Brain Heart Infusion broth (BHI) obtained from BBL (Becton-Dickenson). Samples of pathogenic E. coli strains were obtained from cultures grown overnight in BHI broth then diluted to approximately $10^6$ cfu/ml in 0.1% peptone water. Samples of the comparative non-target strains were enriched in BHI at approximately $10^9$ cfu/ml.

Primers (SEQ ID NOs:2, 3, 5, 6, 8, 9, 10, 11) were prepared by Sigma-Genosys, Woodlands, Tex.

The reagents that were used in the PCR were from BAX® System Reagent Tablet Kits (DuPont Qualicon, Wilmington, Del.) and include SYBR® Green (Molecular Probes, Eugene, Oreg.), Taq DNA Polymerase (Applied Biosystems, Foster City, Calif.), deoxynucleotides (Roche Diagnostics, Indianapolis, Ind.), and buffer (EM Science, New Jersey).

All PCR reactions were carried out using a standard BAX® System (DuPont Qualicon, Wilmington, Del.).

The meaning of abbreviations is as follows: "h" means hour(s), "min" means minute(s), "sec" means second(s), "d" means day(s), "mL" means milliliters.

Examples 1-3

Amplification of Pathogenic E. coli Specific DNA Fragments

Three primer sets (PS1, PS2, PS3) were designed based on sequence analysis of a region of the E. coli O157:H7 genome. One primer set (PS4) is a modification of PS3 that does not alter specificity but does alter the melting temperature of the amplified product. Blast searches of the NCBI database revealed no significant sequence homologies to genes of known function. Primer design was not aided by any software program.

The following cycling conditions were tested with the above mentioned primer sets: 94° C., 2 min initial DNA denaturation, followed by 38 cycles of 94° C., 15 seconds and annealing/extension at 70° C. for 3 minutes.

Multiple *E. coli* strains of pathogenic and non-pathogenic serotypes were tested.

Figure 2:
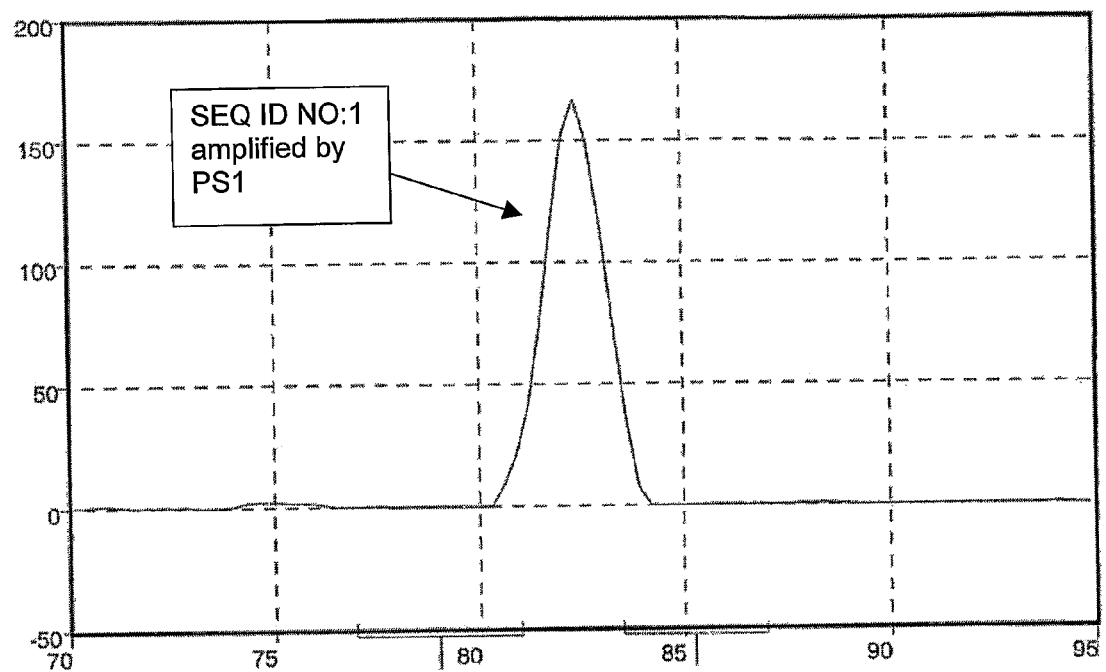
FIG. 2 shows a representative melting curve analysis for a pathogenic *E. coli* O157:H7 positive sample amplified with Primer Set 1 (PS1). The melting curve of the amplified target (SEQ ID NO:1) is at approximately 83° C.

The determination of the presence of SEQ ID NO:1 is a positive PCR achieved with Primer Set 1 (PS1) and DNA melting curve analysis as mentioned above. A positive reaction for Primer Set 1 (PS1) resulted in the appearance of a melting curve peak at approximately 83° C. FIG. 2 shows a representative melting curve analysis for a pathogenic *E. coli* positive for target amplification product (SEQ ID NO:1) amplified with Primer Set 1 (PS1).

Figure 3:
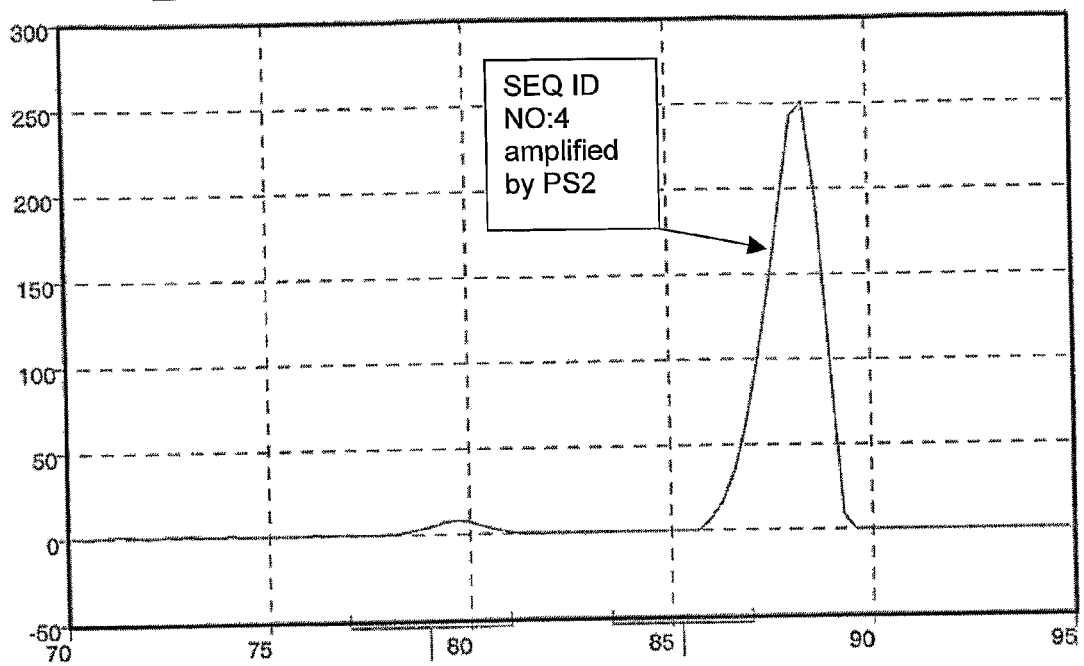
FIG. 3 shows a representative melting curve analysis for a pathogenic *E. coli* O157:H7 positive sample amplified with Primer Set 2 (PS2). The melting curve of the amplified target (SEQ ID NO:4) is at approximately 88° C.

The determination of the presence of SEQ ID NO:4 is a positive PCR achieved with Primer Set 2 (PS2) and DNA melting curve analysis as mentioned above. A positive reaction for Primer Set 2 (PS2) resulted in the appearance of a melting curve peak at approximately 88° C. FIG. 3 shows a representative melting curve analysis for a pathogenic *E. coli* positive for target amplification product (SEQ ID NO:4) amplified with Primer Set 2 (PS2).

Figure 4:
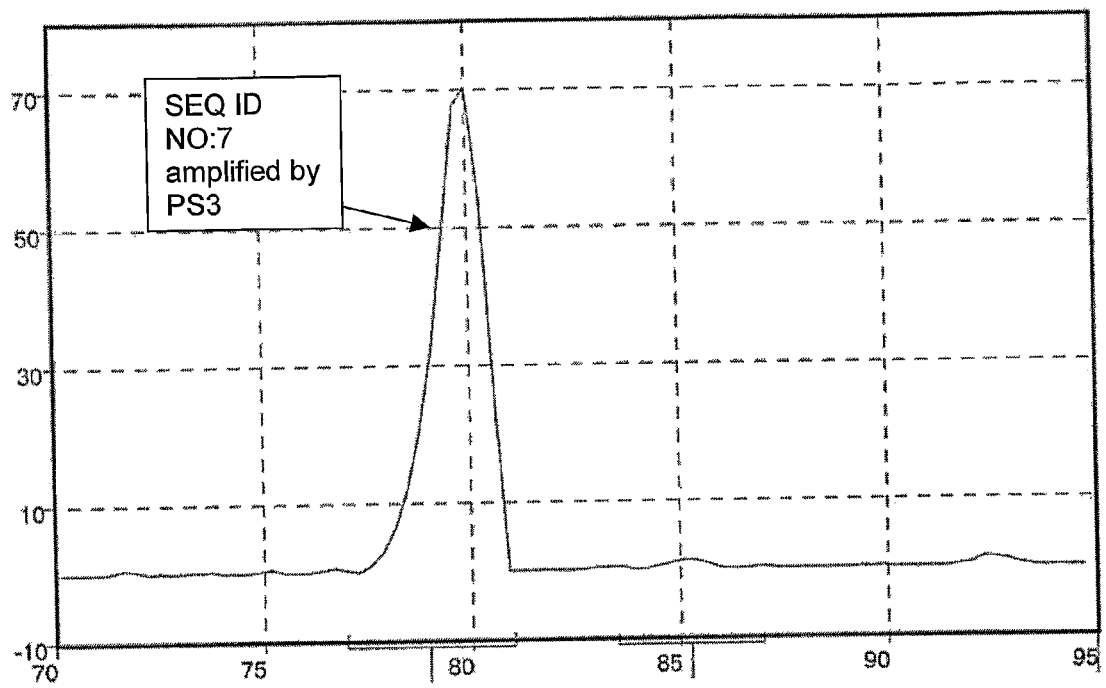
FIG. 4 shows a representative melting curve analysis for a pathogenic *E. coli* O157:H7 positive sample amplified with Primer Set 3 (PS3). The melting curve of the amplified target (SEQ ID NO:7) is at approximately 80° C.

The determination of the presence of SEQ ID NO:7 is a positive PCR achieved with Primer Set 3 (PS3) and DNA melting curve analysis as mentioned above. A positive reaction for Primer Set 3 (PS3) resulted in the appearance of a melting curve peak at approximately 80° C. FIG. 4 shows a representative melting curve analysis for a pathogenic *E. coli* positive for target amplification product (SEQ ID NO:7) amplified with Primer Set 3 (PS3).

Figure 5:
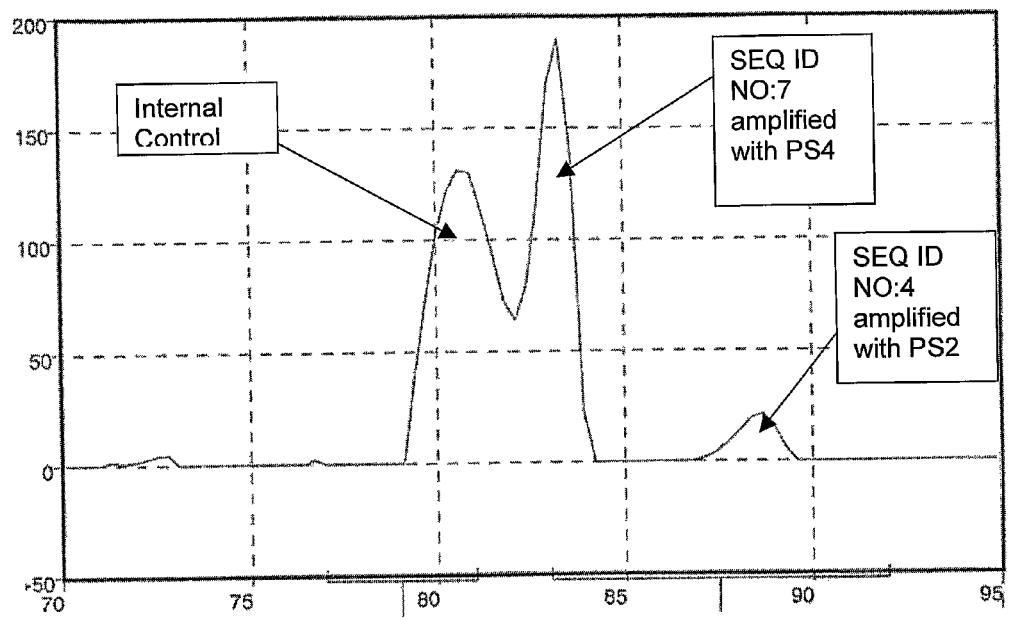
FIG. 5 shows the inclusion of an internal positive control and *E. coli* O157:H7 DNA amplified with Primer Sets 2 (PS2) and Primer Set 4 (PS4). The amplified target (SEQ ID NO:4) from Primer Set 2 (PS2) generates a melting curve at approximately 88° C. Primer Set 4 (PS4), having GC rich additions at the 5' ends, shifts the melting curve of the amplified target (SEQ ID NO:7 with GC additions from the GC clamps) to a higher temperature (approximately 83° C.) vs. SEQ ID NO:7 (approximately 80° C.) so that it can be more readily distinguished from the internal positive control melting curve (approximately 81° C.).

The determination of the presence of SEQ ID NO:7 is a positive PCR achieved with Primer Set 4 (PS4) and DNA melting curve analysis as mentioned above. A positive reaction for Primer Set 4 (PS4) resulted in the appearance of a melting curve peak at approximately 83° C., due to the CC clamps (as explained above, Primer Set PS4 is Primer Set PS3 with GC clamps). FIG. 5 shows a representative melting curve analysis for a pathogenic *E. coli* positive amplified with Primer Set 4 (PS4).

The complete results are set forth in Table II (PS1, Example 1), Table III (PS2, Example 2), and Table IV (PS3 or PS4, Example 3).

TABLE 2

Results for SEQ ID NO: 1 by PCR with Primer Set PS1 (Example 1)

| *E. coli* serotype * denotes pathogenic | Total No. of Strains Tested | No. of Positive PCR Product | No. of Negative PCR Product |
|---|---|---|---|
| O157:H7* | 112 | 112 | 0 |
| O157:HNM* | 3 | 3 | 0 |
| O55:H7* | 3 | 3 | 0 |
| 026:H11* | 9 | 8 | 1 |
| O91:H21* | 1 | 0 | 1 |
| O91:HNM* | 1 | 0 | 1 |
| O113:H11* | 3 | 0 | 3 |
| O146:H21* | 2 | 0 | 2 |
| O45:H2* | 2 | 0 | 2 |
| O103:H2* | 2 | 0 | 2 |
| O125:HNM* | 2 | 0 | 2 |
| O5:HNM* | 2 | 0 | 2 |
| O145:HNM* | 3 | 2 | 1 |
| O1:H7 | 1 | 0 | 1 |
| O113:H7 | 1 | 0 | 1 |
| 02:H7 | 1 | 0 | 1 |
| O25:H7 | 1 | 0 | 1 |
| O157:H19 | 1 | 0 | 1 |
| O55:H10 | 1 | 0 | 1 |

TABLE 3

Results for SEQ ID NO: 4 by PCR with Primer Set PS2 (Example 2)

| *E. coli* serotype * denotes pathogenic | Total No. of Strains Tested | No. of Positive PCR Product | No. of Negative PCR Product |
|---|---|---|---|
| O157:H7* | 112 | 112 | 0 |
| O157:HNM* | 3 | 3 | 0 |
| O55:H7* | 4 | 4 | 0 |
| O26:H11* | 11 | 10 | 1 |
| O26:HNM | 1 | 1 | 0 |
| O91:H21* | 1 | 0 | 1 |
| O91:HNM* | 1 | 0 | 1 |
| O113:H11* | 3 | 0 | 3 |
| O146:H21* | 2 | 0 | 2 |
| O45:H2* | 2 | 0 | 2 |
| O103:H2* | 2 | 0 | 2 |
| O125:HNM* | 2 | 0 | 2 |
| O5:HNM* | 2 | 0 | 2 |
| O145:HNM* | 3 | 2 | 1 |
| O111:HNM* | 3 | 2 | 1 |
| Non Pathogenic isolates representing one each of 93 different serotypes | 93 | 0 | 93 |

TABLE 4

Results for target SEQ ID NO: 7 by PCR with Primer Set PS3 or PS4 (Example3)

| *E. coli* serotype * denotes pathogenic | Total No. of Strains Tested | No. of Positive PCR Product | No. of Negative PCR Product |
|---|---|---|---|
| O157:H7* | 112 | 112 | 0 |
| O157:HNM* | 3 | 3 | 0 |
| O55:H7* | 4 | 4 | 0 |
| O26:H11* | 11 | 0 | 11 |
| O26:HNM | 1 | 0 | 1 |
| O91:H21* | 1 | 0 | 1 |
| O91:HNM* | 1 | 0 | 1 |
| O113:H11* | 3 | 0 | 3 |
| O146:H21* | 2 | 0 | 2 |
| O45:H2* | 2 | 0 | 2 |
| O103:H2* | 2 | 0 | 2 |
| O125:HNM* | 2 | 0 | 2 |
| O5:HNM* | 2 | 0 | 2 |
| O145:HNM* | 3 | 0 | 3 |
| O111:HNM* | 3 | 0 | 3 |
| Non Pathogenic isolates representing one each of 93 different serotypes | 93 | 0 | 93 |

Example 4

Use of Multiple Primer Sets and an Internal Control in the Same PCR Reaction

FIG. 5 shows a sample in which an internal positive control was added. The internal positive control melts out at approximately 77-78° C., which is clearly distinguishable from the pathogenic *E. coli* amplicons of two primer sets employed, namely, both Primer Set 4 (PS4) (in lieu of Primer Set 3 (PS3) for the detection of SEQ ID NO:7), resulting in a melting point curve peak at approximately 83° C., and Primer Set 1 (PS2) for the detection of SEQ ID NO:4, resulting in a melting point curve peak at approximately 88° C.

What is claimed is:

1. A method for detecting the presence of pathogenic *E. coli* in a sample, the method comprising:
   (a) performing PCR amplification of the sample using a primer pair selected from the group consisting of:
      (i) SEQ ID NOs:2 and 3,
      (ii) SEQ ID NOs:5 and 6,
      (iii) SEQ ID NOs:8 and 9,
      (iv) SEQ ID NOs:10 and 11,
      (v) SEQ ID NOs:13 and 14, and
      (vi) SEQ ID NOs:16 and 17,
      to produce a PCR amplification result; and
   (b) examining the PCR amplification result of step (a) to detect for an amplification product of the primer pair, whereby a positive detection of the amplification product of the primer pair indicates the presence of pathogenic *E. coli* in the sample.

2. The method of claim 1, wherein the primer pair is selected from the group consisting of (a)(ii), (a)(iii), and (a)(iv).

3. The method of claim 1, wherein the primer pair comprises (a)(ii).

4. The method of claim 1, wherein the primer pair comprises (a)(iii).

5. The method of claim 1, wherein the primer pair comprises (a)(iv).

6. A method for detecting the presence of pathogenic *E. coli* in a sample, the method comprising:
   (a) performing PCR amplification of the sample using two different primer pairs selected from the group consisting of:
      (i) SEQ ID NOs:2 and 3,
      (ii) SEQ ID NOs:5 and 6,
      (iii) SEQ ID NOs:8 and 9,
      (iv) SEQ ID NOs:10 and 11,
      (v) SEQ ID NOs:13 and 14, and
      (vi) SEQ ID NOs:16 and 17,
      to produce a PCR amplification result; and
   (b) examining the PCR amplification result of step (a) to detect for amplification products of both of the two different primer pairs, whereby a positive detection of the amplification products of both of the two different primer pairs indicates the presence of pathogenic *E. coli* in the sample.

7. The method of claim 6, wherein the two primer pairs comprise (a)(ii) and (a)(iv).

8. The method of claim 6, wherein the two primer pairs comprise (a)(ii) and (a)(iii).

9. The method of claim 1 or 2, wherein in step (b) a melting curve analysis is used to detect for amplification product.

10. The method of claim 1 or 2, further comprising a step of preparing the sample for PCR amplification prior to said step (a).

11. The method of claim 10, wherein said preparing step comprises at least one of the following processes: (1) bacterial enrichment, (2) separation of bacterial cells from the sample, (3) cell lysis, and (4) total DNA extraction.

12. The method of claim 1 or 2, wherein the sample comprises a food sample or a water sample.

13. The method of claim 1 or 2, wherein the sample comprises a selectively enriched food matrix.

14. A primer for use in primer directed amplification for detection of pathogenic *E. coli* consisting essentially of SEQ ID NO:2, SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:16, or SEQ ID NO:17.

15. A kit for detection of pathogenic *E. coli*, comprising:
(a) at least one primer pair selected from the group consisting of:
(i) SEQ ID NOs:2 and 3,
(ii) SEQ ID NOs:5 and 6,
(iii) SEQ ID NOs:8 and 9,
(iv) SEQ ID NOs:10 and 11,
(v) SEQ ID NOs:13 and 14, and
(vi) SEQ ID NOs:16 and 17; and
(b) thermostable DNA polymerase.

16. The kit of claim 15, wherein component (a) comprises both (a)(ii) and (a)(iv).

17. The kit of claim 15, wherein component (a) comprises both (a)(ii) and (a)(iii).

18. A replication composition for use in performance of PCR, comprising:
(a) at least one primer pair selected from the group consisting of:
(i) SEQ ID NOs:2 and 3,
(ii) SEQ ID NOs:5 and 6,
(iii) SEQ ID NOs:8 and 9,
(iv) SEQ ID NOs:10 and 11,
(v) SEQ ID NOs:13 and 14, and
(vi) SEQ ID NOs:16 and 17; and
(b) thermostable DNA polymerase.

19. The replication composition of claim 18, wherein component (a) comprises both (a)(ii) and (a)(iv).

20. The replication composition of claim 18, wherein component (a) comprises both (a)(ii) and (a)(iii).

21. A tablet comprising the replication composition of claim 18, 19, or 20.

22. A kit for detection of pathogenic *E. coli* in a sample, comprising the tablet of claim 21.

* * * * *